United States Patent [19]

Briggs et al.

[11] Patent Number: 4,579,982

[45] Date of Patent: Apr. 1, 1986

[54] PREPARATION OF MONOALKYLENE GLYCOLS USING TWO LIQUID PHASE REACTION MENSTRUUM

[75] Inventors: John R. Briggs; John H. Robson, both of Charleston, W. Va.

[73] Assignee: Union Carbide Corporation, Danbury, Conn.

[21] Appl. No.: 594,385

[22] Filed: Mar. 28, 1984

[51] Int. Cl.$^4$ ............ C07C 31/20; C07C 33/26; C07C 35/14; C07C 33/035

[52] U.S. Cl. .................. 568/867; 568/811; 568/833; 568/857

[58] Field of Search ............ 568/867, 833, 811, 857

[56] References Cited

U.S. PATENT DOCUMENTS

| | | | |
|---|---|---|---|
| 2,141,443 | 12/1938 | Stanley et al. | 260/614 |
| 2,807,651 | 9/1957 | Britton et al. | 260/611 |
| 3,028,434 | 4/1962 | Weltz et al. | 260/635 |
| 3,062,889 | 11/1962 | Murphy | 260/601 |
| 3,475,499 | 10/1969 | Winnick | 260/615 |
| 3,778,451 | 12/1973 | Poite | 260/348.5 L |
| 3,992,432 | 11/1976 | Napier et al. | 260/465.1 |
| 4,107,221 | 8/1978 | Tasto et al. | 260/652 P |
| 4,160,116 | 7/1979 | Mieno et al. | 568/867 |
| 4,165,440 | 8/1979 | Kim | 568/867 |
| 4,277,632 | 7/1981 | Kumazawa et al. | 568/700 |
| 4,283,580 | 8/1981 | Odanaka et al. | 568/858 |

FOREIGN PATENT DOCUMENTS

| | | | |
|---|---|---|---|
| 54-128507 | 10/1979 | Japan . | |
| 73035 | 6/1981 | Japan | 568/867 |
| 56-73036 | 6/1981 | Japan . | |
| 56-92228 | 7/1981 | Japan . | |

OTHER PUBLICATIONS

U.S.P.A. Ser. No. 530,235 filed 9/8/83.
U.S.P.A. Ser. No. 594,264 filed 3/28/84.
U.S.P.A. Ser. No. 594,268 filed 3/28/84.

Primary Examiner—J. E. Evans
Attorney, Agent, or Firm—Steven T. Trinker

[57] ABSTRACT

Alkylene oxides are hydrolyzed in a reaction menstruum containing an aqueous phase, a water-immiscible liquid phase, and a selectivity-enhancing, dissociatable metalate anion-containing material. The concentration of the metalate anion-containing material is greater in the water-immiscible liquid phase than that in the aqueous phase. The water-immiscible liquid phase can be separated from the aqueous phase to recover metalate anion-containing material.

26 Claims, No Drawings

PREPARATION OF MONOALKYLENE GLYCOLS USING TWO LIQUID PHASE REACTION MENSTRUUM

This invention relates to processes for the preparation of monoalkylene glycols from alkylene oxides and water involving the use of selectivity-enhancing, dissociatable metalate anion-containing material. The processes of this invention enable the production of monoalkylene glycols with high selectivity. In the processes of this invention, a reaction menstruum containing an aqueous phase and a water-immiscible liquid phase having a greater concentration of the metalate anion than such concentration in the aqueous phase is employed. Advantageously, the processes of this invention facilitate the recovery of metalate anion from the alkylene glycol product and water. This separation can, for instance, be effected through phase separation and thereby enhance the commercial viability of using metalate anion in the production of monoalkylene glycol.

INTRODUCTION TO ALKYLENE GLYCOLS

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

The hydrolysis reaction proceeds uncatalyzed; however, the presence of acids or bases enhances the rate of reaction. Acid and base catalysts, however, do have shortcomings. For instance, base catalysts are generally not selective to the formation of the monoglycol product and acid catalysts are typically associated with corrosion problems. Hence, commercial processes typically utilize relatively neutral hydrolysis conditions (for instance, pH 6-10).

Representative of the numerous acid catalysts that have been suggested for use in the hydration of alkylene oxides include fluorinated alkyl sulfonic acid ion exchange resins (U.S. Pat. No. 4,165,440, issued Aug. 21, 1979); carboxylic acids and halogen acids (U.S. Pat. No. 4,112,054, issued Sept. 5, 1978); strong acid cation exchange resins (U.S. Pat. No. 4,107,221, issued Aug. 15, 1978); aliphatic mono- and/or polycarboxylic acids (U.S. Pat. No. 3,933,923, issued Jan. 20, 1976); cationic exchange resins (U.S. Pat. No. 3,062,889, issued Nov. 6, 1962); acidic zeolites (U.S. Pat. No. 3,028,434, issued Apr. 3, 1962); sulfur dioxide (U.S. Pat. No. 2,807,651, issued Sept. 24, 1957); trihalogen acetic acids (U.S. Pat. No. 2,472,417, issued June 7, 1949); and copper-promoted aluminum phosphate (U.S. Pat. No. 4,014,945, issued Mar. 29, 1977).

In addition to the acid catalysts, numerous catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Pat. No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Various metal-containing compounds, including metal oxides, have been proposed as catalysts for the hydrolysis of alkylene oxides. For example, U.S. Pat. No. 2,141,443, issued Dec. 27, 1938, discloses the production of glycols by the reaction of alkylene oxide with water in the presence of a dehydrating metal oxide, for example, alumina, thoria, or oxides of tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water followed by drying the catalyst. Similarly, U.S. Pat. No. 2,807,651, issued Sept. 24, 1957, states that it is known to catalyze the reaction of an alkylene oxide and water by alkali metal bases, alcoholates, oxides of titanium, tungsten and thorium.

Many metals such as vanadium, molybdenum, tungsten, titanium, chromium, zirconium, tantalum, rhenium, and niobium, have also been proposed as components in catalysts for preparing 1,2-epoxides of alpha-olefins and organic hydroperoxides. Often these catalysts are present during a subsequent hydrolysis reaction. For instance, Examples I and III or U.S. Pat. No. 3,475,499, issued Oct. 28, 1969, disclose that a mixture of normal alpha-olefins containing 11 to 15 carbon atoms was epoxidized with ethylbenzene hydroperoxide in the presence of molybdenum naphthanate catalyst. After distillation, the bottoms which contained the 1,2-epoxides and the molybdenum-containing catalyst were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal salts, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228, published July 25, 1981, is directed to processes for producing highly pure alkylene glycols. The disclosure is directed to a distillation procedure for recovery of a molybdenum and/or tungsten-containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

U.S. patent applications Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It is also disclosed that the vanadate may be introduced into the reaction system in the salt form or on a support such as silica, alumina, zeolites and clay. Since the vanadate ion is water soluble, it can be lost from the reaction system and means must be provided to recover it from the effluent from the reaction zone.

The processes specifically exemplified in, for instance, U.S. Pat. No. 4,277,632 and Japanese Kokai Nos. JA 54/128,507, JA 56/073,035, 56/073,036, and 56/92228 employ a single phase reaction menstruum in which the catalyst is apparently dissolved. In order to provide monoalkylene glycol or merchantable quality, especially polyester grade ethylene glycol, as well as to provide a commercially viable process, the catalyst should be separated from the alkylene glycol products in a form suitable to enable the catalyst to be recycled to the process. Heretofore, fractional distillation procedures have been suggested for the recovery of certain of these catalysts. However, the stability of the catalysts during such distillation has been noted as a particular problem. In Japanese Kokai Nos. 56/92228 and 56/118024 (published Sept. 16, 1981), the disclosures state that during recovery of a molybdenum-containing catalyst by distillation, a molybdenum hydrate can be formed which precipitates, thereby increasing handling difficulties and rendering the catalyst less active. Moreover, the pH of the distillation column is made alkaline and ethylene glycol is oxidized by the reduction of the molybdenum-containing catalyst, both of which adversely affect the quality of the glycol product. The disclosures specifically provide for the addition of water to the still bottoms for the purpose of stabilizing the catalyst. Recovering the catalyst by fractional distillation thus not only provides the problem of energy consumption since the glycol products must be separated as a vapor from the higher boiling catalyst, but also the catalyst may be unstable and affect the quality of the glycol products.

Copending U.S. patent application Ser. No. 594,268, filed on even date herewith, of R. D. Best, J. A. Collier, B. T. Keen and J. H. Robson, is directed to processes for the hydrolysis of alkylene oxide in the presence of selectivity-enhancing metalate anion which is in association with electropositive complexing sites on a solid support. Readily available solids include anion exchange resins.

OVERVIEW OF THE INVENTION

The processes of this invention relate to making alkylene glycols by the hydrolysis of alkylene oxide with water using selectivity-enhancing, dissociatable metalate anion-containing material in a reaction menstruum containing two liquid phases. In the reaction menstruum is provided an aqueous phase and a water-immiscible liquid phase wherein the concentration of the metalate anion-containing material in the water-immiscible phase is greater than the concentration in the aqueous phase. Preferably, essentially all of the metalate anion-containing material is provided in the water-immiscible phase.

It has been found that even though the metalate anion-containing material is in the non-aqueous phase, high selectivities to the monoalkylene glycol can still be obtained. Advantageously, since metalate anion-containing material is provided in the water-immiscible phase, the recovery of the material from the alkylene glycol product, which is soluble in the aqueous phase, is facilitated and can readily be conducted under conditions that do not unduly adversely affect the metalate anion or the quality of the glycol product.

This invention thus provides processes for making alkylene glycols with enhanced selectivities to the formation of monoalkylene glycols wherein the recovery of the metalate anion-containing material is facilitated without detriment to the activity of the metalate anion or the quality of the glycol products. Moreover, the processes may enable the use of metalate anions, such as the vanadates, that are even more subject to instability than molybdate or tungstate.

In aspects of this invention, the molar ratio of water to alkylene oxide can be substantially reduced from those ratios employed in conventional processes, thereby offering the potential of reduced energy consumption in the recovery of the alkylene oxide from the aqueous phase. Furthermore, despite the reduction in the amount of water employed, undue temperatures in the reaction zone during the exothermic hydrolysis need not be generated since the water-immiscible phase provides additional heat capacity. Accordingly, the processes of this invention offer considerable design flexibility for integrated hydrolysis operations including retrofit applications into existing, conventional alkylene glycol manufacturing facilities.

DISCUSSION RELATING TO THE REACTANTS

Alkylene oxides which may be used to produce alkylene glycols in the processes of this invention are vicinal alkylene oxides having the general formula:

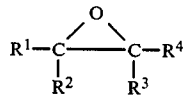

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organohydroperoxide in the presence of a catalyst or by the partial oxidation of an alkene with a molecular oxygen-containing gas in the presence of a silver catalyst.

Water (as the liquid or steam) is also employed as a reagent for the formation of the corresponding alkylene glycol. Usually the water is of sufficient purity to provide a suitable quality alkylene glycol product. Liquid water may be distilled or demineralized, for example, by ion exchange treatment.

The metalate anions are characterized by an anionic structure containing at least one metal atom and at least one oxygen ligand that is conventionally characterized as a double-bonded oxygen atom.

The metalate anions which may be useful in the processes of this invention comprise a polyvalent metal having a positive functional oxidation state, often an oxidation state of at least +3, say, +4 to +6 or +7, and may be a transition metal. The metalate anions may be illustrated by the following formula:

$$[(A)_q M(O)]^{a-}$$

wherein $a-$ is the negative charge of the anion which is usually between $-1$ and $-4$, A is one or more substituents to fill the remaining valencies (q) of M and may be the same or different and may be, for instance, double bonded oxygen; an organic radical such as an alkyl, alkoxy, acyl, aryl, amino, phosphino, etc., usually of 1 to about 12 carbon atoms; halogen (e.g., chlorine, fluorine, iodine); —O— or —S— wherein the remaining valency of the oxygen atom is in free ionic form or is bonded to a metal atom (as in a bimetal or polymetal-containing metalate) or cation. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals such as rhenium and germanium may also find application. Representative metalate anions which are especially useful include molybdate, tungstate, metavanadate, hydrogen pyrovanadate and pyrovanadate (although because of the complex chemistry associated with many metalate anions, the precise structure of the operative specie or species may be different). Frequently the metalate anion comprises at least one anion conventionally characterized by the formulae $[MoO_4]^{2-}$, $[VO_3]^{-}$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the added metalate anion) appear to exhibit little, if any, activity for enhancing selectivity.

Advantageously, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as in rhenate anion under the same conditions. Also, it is frequently the case that the metal as the metalate has an eletrophilicity with respect to ethylene oxide greater than that exhibited by vanadium as in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenate with respect to ethylene oxide. If the production of diethylene glycol and polyethylene glycol is greater than that provided with orthovanadate, regardless of the rate of formation of ethylene glycols, then the metal as the metalate is probably less electrophilic than orthovanadate with respect to ethylene oxide.

The metalate anions are associated with a cation and are dissociatable from the cation. Although the cations may be substantially insoluble, or have little solubility, in water at reaction conditions, the metalate anion can provide the enhanced selectivity to monoalkylene glycol. However, if the metalate anion is too tightly bound, it will not have the desired activity. Thus, calcium vanadate, which has little solubility in water and retains the metalate anion tightly bound, has not been found to be an acceptable metalate-containing compound.

In accordance with one aspect of the invention, the cations render the metalate-containing material preferentially soluble in an organic medium as compared to water. Often, the metalate-containing material will have a greater solubility in a given water-immiscible organic solvent, such as toluene, than in distilled water at a given temperature, say, 25° C. In some instances, the solubility coefficient is at least about 5 times, say, at least about 20 times, greater in toluene than the solubility in distilled water at 25° C.

In another aspect of the invention, the metalate-containing material is substantially insoluble in distilled water, e.g., less than about 50, say, less than 10, grams of the metalate-containing material will dissolve in one liter of water at 25° C. Some metalate-containing materials are immiscible with water and some are solid at ambient temperatures, for instance, 25° C., or even at temperatures suitable for the processes of this invention, e.g., about 50° to 250° C.

Particularly useful metalate-containing materials are those having organic-containing cations (hereinafter referred to as organometalates).

Organometalates may be represented by the formula:

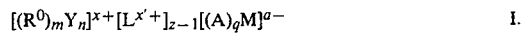

wherein $[(R^0)_m Y_n]^{x+}$ is an organic-containing cation having a positive charge of x and Y is a polyvalent element, which is an ionic charge carrying center, $R^0$ is hydrogen or hydrocarbyl-containing substituent with the proviso that the organic-containing cation has at least one $R^0$ which contains a hydrocarbyl substituent, m is the average number of electron pairs shared by Y with the total $R^0$ groups, n is the number of charge carrying centers, wherein m, n and x are related by the equation $x = n(V-m)$ in which V is the average functional oxidation state of Y wherein each electron pair used by each Y in bonding to $R^0$ is given the value of 1 and the functional oxidation state of Y is the sum of the electron pairs bonding to $R^0$ and x/n, wherein x is an integer of 1 or 2; wherein L is a cation which has a positive charge of x' and which may be the same or different from the organic-containing cation, where x' is usually 1 or 2; wherein z is the number of organic-containing cations which is from 1 to 3. Hence, the negative charge, a, of the metalate anion equals the amount of $x + [(z-1)(x')]$.

The hydrocarbyl-containing substituents useful in the organic-containing cation frequently contain at least four carbon atoms, and may be further substituted with moieties that are not reactive with the anion.

L may be any suitable cation and often is another organic-containing cation or a non-organic-containing cation which serves to balance the charge of the anion. L may include alkali metals, alkaline earth metals, copper, zinc, iron, ammonium cations, phosphonium cations, sulfonium cations, and other cations including organic-containing cations, e.g., containing alkyl, alkoxy, acyl, aryl, amino, phosphino, etc., groups of 1 to about 12 carbons.

Suitable cations may include structures represented by the formulae:

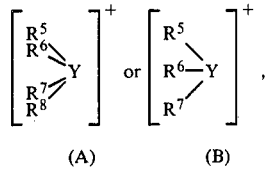

where Y is nitrogen, phosphorous, or arsenic for formula A, or sulfur for formula B, i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in copending U.S. patent application Ser. No. 594,264, filed on on even date herewith, of J. R. Briggs and J. H. Robson, herein incorporated by reference.

Organic-containing cations which may be useful include the bis(hydrocarbyl-phosphine) iminiums represented by the formula

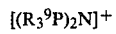

wherein each $R^9$ may be the same or different and may be the same as set forth for $R^5$ to $R^8$. Illustrative iminiums are disclosed in Ser. No. 594,264.

Illustrative of the organic-containing cations are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like; bis(hydrocarbyl phosphine)iminiums such as bis(triphenyl-phosphine)iminium, bis(tribenzyl-phosphine)iminium, bis(trimethylphosphine)iminium, bis(tridodecyl-phosphine)iminium, and the like; quaternized diamines such as N,N'-bis(trimethyl)propylene diamine, N,N'-bis(triphenyl)propylene diamine, N,N'-bis(trioctadecyl)propylene diamine; and quaternized diphosphines such as P,P'-bis(trimethyl)propylene diphosphine, and the like.

The metalate anion may be provided to the reaction mixture as a metalate anion or in a form which is converted to the desired metalate anion by subsequent chemical reaction. Hence, halide, sulfide, or the like, metal-containing compounds may be employed as the precursor to the desired metalate anion. Some of these precursor compounds may be converted to metalates during the hydrolysis reaction.

The metalate may be used in the salt form or may be introduced into the reaction system on a support, such as on a carrier such as silica, alumina, molecular sieves, zeolites, clay, and the like. When the process is carried out, the metalate is generally in a dissolved, mixed, suspended, or deposited form in a fixed bed in a liquid phase. The metalate may be provided to the reaction system by mixing it with alkylene oxide being introduced into the reaction system, it may be introduced by means of a separate inlet to the reaction system, or it may be retained in the reaction zone in an immiscible organic phase. When the organometalate is water-soluble, replenishing the reaction zone is desired. The exact means of introduction of the metalate is not critical, and frequently the metalate is provided at the beginning of the reaction and/or is continuously or intermittently added at a fixed rate during the reaction.

FORMATION OF ALKYLENE GLYCOLS

In the processes of this invention, alkylene oxide is contacted with water in a water-containing reaction menstruum that comprises an aqueous phase and a water-immiscible liquid phase.

The processes may be conducted in any suitable manner for reactions in menstruum containing more than one phase. For instance, the aqueous phase may provide the continuous phase or the water-immiscible phase may be the continuous phase. In general, it is desired that the discontinuous phase is highly dispersed and is in the form of small bubbles to enhance the interface areas between the phases. For example, the discontinuous phase can have bubble diameters of less than about 2, say, less than about 1, e.g., about 0.01 to 0.5, centimeters. Devices to enhance the dispersion may be employed such as agitators, spargers and the like. However, in order to obtain an enhanced selectivity to monoalkylene glycol, it is not usually essential to have a dispersed phase. Indeed, the phases may form adjacent layers during conducting the reaction.

The relative amounts of the aqueous phase and the water-immiscible liquid phase may vary widely, for instance, from 1000:1 to 1:1000 on a volume basis. Usually, the amount of the aqueous phase is selected in respect to the amount of alkylene oxide employed in the process since it is a reactant and must be separated from the alkylene glycol products. Although in conventional alkylene oxide hydrolysis processes the unreacted water serves as a heat sink to assist in maintaining desired temperatures during the exothermic hydrolysis reaction, in the processes of this invention such considerations are often of less importance since the water-immiscible phase provides some degree of heat sink capacity. The mole ratio of water (which under the conditions of the process may be provided in liquid form or steam) to alkylene oxide is often in the range of about 0.5:1 to 50:1, and preferably, the amount of water employed is at least sufficient on a stoichiometric basis to react with all the alkylene oxide provided, e.g., the mole ratio is at least 1:1 up to, say, about 40:1 or 50:1, say, about 1:1 to 20:1.

It is believed that the hydrolysis reaction in the processes of this invention can proceed by at least two routes, one involving the selectivity-enhancing metalate and the other being the conventional route. Thus, the processes of this invention are capable of producing dialkylene glycol and higher glycols. Hence, the lower the ratio of water to alkylene glycol, all other factors remaining the same, the greater the amount of these dialkylene and higher glycols that will be produced. This provides a degree of flexibility in operating processes of the invention to provide a desired amount of these higher glycols but an amount less than would be obtained in a conventional process. In most instances, the mole ratio is in the range of about 3:1 to 10:1 (mole basis).

Another factor affecting the degree of selectivity to the monoalkylene glycol is the amount of metalate anion employed. Generally, the greater the amount of metalate anion employed, the higher the selectivity to monoalkylene glycol, all other factors remaining the same. Thus, the mole ratio of metalate anion to alkylene oxide may be up to 5:1 or 10:1 or more. Economics usually dictate that the mole ratio of metalate anion to alkylene oxide will be less than about 2:1. Often, the mole ratio is at least about 0.001:100, say, in the range of about 0.05:100 to 2:1, e.g., about 0.1:100 to 1:1, and most frequently about 1:100 to 0.5:1. For purposes of determining the moles of metalate anion present, in respect to anions containing more than one site which is available for association with alkylene oxide, e.g., molybdate and tungstate, the moles shall be calculated based on the number of such sites.

The metalate anion-containing material may itself form the water-immiscible phase, or it may be in combination with one or more substantially water-insoluble components, e.g., solvents such as water-immiscible organic liquids, in which the metalate anion-containing material is dissolved. The solvent is preferably non-reactive with alkylene oxide and the metalate anion-containing material. However, in some instances it may be desirable to use interactive solvents such as 1,2-dimethoxyethane in addition to the substantially water-insoluble solvent. The preferred solvents are those in which the metalate anion-containing material is preferentially soluble in comparison to water under the conditions of the hydrolysis reaction. Frequently, the metalate anion-containing material is at least about 5 times more soluble in the solvent than in water at 25° C. This characteristic of the solvent facilitates the recovery of the metalate anion-containing material from the glycol-containing aqueous phase. Often the metalate anion-containing material is highly soluble in the solvent. Usually, at 25° C., it is soluble in the solvent in an amount of at least about 50 grams per liter.

Exemplary of liquid solvents are alkyl, cycloalkyl and aromatic-containing solvents, especially halogenated alkyl, cycloalkyls and aromatics, such as cyclopentane, cyclohexane, methylcyclohexane, cycloheptane, benzene, toluene, xylene, naphthene, dichloromethane, 1,1,2-trichloroethane and the like. Also, silicone oils and mineral oils may be useful. Not all the above solvents will be suitable for all of the processes of this invention.

The water-immiscible liquid phase may be denser or less dense than water. Often, the density of the water-immiscible liquid phase is sufficiently different than that of the aqueous phase to facilitate phase separation, e.g., the densities may differ by at least about 0.05, say, at least about 0.1, gram per cubic centimeter under the conditions of the hydrolysis reaction.

The amount of solvent, when employed, can vary widely and is frequently in the range of about 0.1:1 to 10:1 volumes per volume of water. The amount of solvent employed is often determined based upon the solubility of the metalate anion-containing material in the solvent, whether the water-immiscible phase is to be the continuous phase, the desired mass for the dissipation of heat from the exothermic hydrolysis reaction, and the like.

The hydrolysis can be conducted under conditions sufficient to maintain the aqueous phase and the water-immiscible phase as liquids and to effect the hydrolysis. The temperature, however, should not be so great that the metalate anion-containing material is unduly adversely affected. Frequently, the reaction temperature is between about 20° C. and about 220° C. or 250° C., say, between about 50° C. and 200° C., and sometimes between about 80° C. and 180° C.

The processes may be conducted at subatmospheric, atmospheric or superatmospheric pressure. For purposes of convenience, the reaction is typically conducted at pressures greater than ambient, e.g., between about 0.1 and 1000 kilograms per square centimeter gauge, and preferably between about 2 and 100 kilograms per square centimeter gauge.

The hydrolysis may be conducted for a time insufficient for complete reaction, but it is generally preferred that when water is provided in amounts sufficient for complete reaction with the alkylene oxide, the reaction is conducted for a period of time sufficient to ensure that substantially all the alkylene oxide is reacted. The amount of time required to accomplish the substantially complete reaction is determined by the other conditions employed including temperature, amount of reactants present, and the like. The reaction may be carried out for very short periods of time; e.g., fractions of a second, and, if desired, may be carried out for periods of up to hours, e.g. about 0.01 second to 5 hours, preferably about 1 second to 30 minutes.

The alkylene oxide may be a gas under the conditions of the reaction and may be introduced into the liquid medium as a fine dispersion of gas bubbles, but, most frequently, the pressure is sufficient to maintain the alkylene oxide in the liquid phase.

The hydrolysis may be conducted in the presence of a gas, which is preferably inert. Gases which may be employed include air, carbon dioxide, nitrogen, argon and the like. Carbon dioxide is often present by the very nature of the process and the source of the alkylene oxide (especially by partial oxidation of alkenes). Frequently, it is desired to maintain the mole ratio of carbon dioxide to alkylene oxide less than 0.1:1, particularly less than 0.05:1, unless it is desired to affect the pH of the reaction menstruum.

The pH of the reaction menstruum is frequently maintained relatively neutral, e.g., between about 5 and 11, preferably about 6 to 10.5, and most often the pH is in the range of about 6 to 10. With some metalate anions, such as the vanadates, tungstates and molybdates, the pH of the medium can be determinative of the species present. For example, in strong bases the orthovanadate may predominate, but at neutral conditions metavanadate may predominate. In another example, more acidic media promote the formation of polynuclear molybdates which often have less, if any, activity towards forming the associated moiety.

The pH may be maintained within the desired range by the addition of acid or base, or the addition of buffers, as is well known in the art. However, the presence and nature of salts should be considered since the cation may displace the cation for the metalate anion. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor.

The maintenance of the pH within the desired ranges can also have a secondary effect of enhancing the stability of the metalate anion.

The stability of organometalates when used in processes in accordance with this invention may be enhanced by the addition of small quantities of metalate anion-containing material to the water-immiscible phase. The added metalate anion is often provided in amounts less than 1000 ppm by weight with a mole ratio of added metalate anion to organometalate of about 1:50 to 1:1000. The added metalate anion-containing material can conveniently be provided as a more water-soluble salt, e.g., sodium or potassium metalate. See U.S. patent application Ser. No. 594,267, filed on event date herewith, of B. T. Keen, herein incorporated by reference, for further discussion.

The processes of this invention may be conducted batch-wise, semi-continuously or continuously using suitable processing equipment. For example, the reaction may be conducted in a vessel provided with means to promote the contact between the phases, e.g., agitators, packing, trays, spargers, or the like. The feed, or various components, may be premixed before being introduced into the reactor or the components may be separately introduced into the reaction vessel. For instance, a water-immiscible liquid phase can be admixed with alkylene oxide and introduced into an aqueous phase in the reaction vessel. Alternatively, alkylene oxide may be separately introduced into a reaction vessel containing a water-immiscible liquid phase and an aqueous phase. In any event, the process should be operated such that at least a portion of the alkylene oxide has an opportunity to contact the substantially water-insoluble phase containing the metalate anion-containing material prior to reaction with water.

It is usually desired to separate the alkylene glycol product from the reaction menstruum and to recover the metalate anion-containing material for further use in the process. Since the alkylene glycol is usually preferentially soluble in a liquid, aqueous phase, the glycol products can be removed by phase separation (e.g., decanting, centrifugation) from the water-immiscible phase and then recovered. The alkylene glycol-rich aqueous phase can be refined to recover high purity monoalkylene glycol, for instance, by the use of multiple effect evaporators to remove water and distillation, e.g., vacuum distillation, to refine the monoalkylene glycol from higher glycol impurities and other impurities. The metalate anion-containing material within the separated, water-immiscible phase can be recycled for further use.

In some instances, the separated aqueous phase may contain some dissolved metalate anion-containing material after the phase separation. If desired, this metalate anion-containing material may be recovered by suitable techniques. For example, the metalate anion-containing material can be extracted from the aqueous phase by contact with an immiscible liquid in which the metalate anion or its associated cation is preferentially soluble. For further discussion see U.S. patent application Ser. No. 594,266, filed on even date herewith, of B. T. Keen, et al., herein incorporated by reference. Alternatively, the aqueous phase may be contacted with, for instance, an anion exchange resin such as a chloride-loaded DOWEX (TM) MSA-1 resin available from the Dow Chemical Company to recover the metalate anion. This resin can be separated and regenerated with the recovery of the metalate anion. See, for further discussion, U.S. patent application Ser. No. 594,269, filed on even date herewith, of J. A. Collier, herein incorporated by reference. It is also possible to recover the metalate anion-containing material by distillation (e.g., evaporation or fractional distillation) from the alkylene glycols. When employing higher temperature separation processes, e.g., above about 100° or 120° C., the provision of small amounts of water enhances the stability of many metalate anions.

The following examples are provided to assist in the understanding of the invention and are not in limitation thereof. All percentages and parts of solids are by weight and all percentages and parts of liquids and gases are by volume unless otherwise indicated.

The analyses of the reaction products were conducted by temperature programmed gas chromatography. One method used a 10 ft × ⅛" stainless steel column packed with Chromosorb 101 (TM) (60/80 mesh). Sample injections (2–3 microliters) were made from a sample of 1.5 to 2.0 grams of hydrolysis product to which had been added 0.12 to 0.15 gram of 2-ethyl-1,3-hexanediol as internal standard.

In another method, the samples are prepared by adding about 2 weight percent 1,3-butanediol as an internal standard. Approximately 50 microliters of this admixture are added to 1.0 milliliter of Regisil (TM) (BSTFA) (N,N-bis trimethylsilyl trifluoroacetamide), available from the Regis Chemical Company, Morton Grove, Ill., in a serum vial and mixed for at least about 12 hours. The weight percent monothylene glycol, diethylene glycol and triethylene glycol are determined by standard vapor phase chromatography using a Hewlett Packard 5880 (TM) gas chromatograph equipped with a four meter by ⅛ inch (0.32 centimeters) (outside diameter) stainless steel column packed with 20 percent OV-101 methylsilicone stationary liquid phase supported on 80/100 mesh Chromosorb W HP (TM) both available from Supelco, Inc. Bellefonte, Pa.

Selectivities are defined as $[G/(M+D+T)]$ times 100% where G is the weight of the glycol in question, M is the weight of monoalkylene glycol, D is the weight of dialkylene glycol and T is the weight of trialkylene glycol.

Unless otherwise stated, the examples were conducted using a 300 milliliter Parr reactor.

EXAMPLE 1

The reactor was charged with 16.04 grams of ethylene oxide, 16.19 grams of distilled water, 2.92 grams of bis[tetra-n-hexyl)ammonium] molybdate and 26.24 grams of toluene. A two-phase reaction medium resulted and the mixture was continuously stirred to maintain a dispersion of the phases. The reaction medium was heated to about 140° C. for slightly over one hour. During the reaction, the pressure increased to about 160 psig and then fell to about 40 psig. The reactor was cooled with cooling water and then ice water to about 5° C. and opened. The aqueous layer was recovered and analyzed to contain monoethylene glycol (89% selectivity), diethylene glycol (11% selectivity), and triethylene glycol (less than 1% selectivity).

EXAMPLE 2

The reactor was charged with 15.4 grams of ethylene oxide, 15.4 grams of distilled water, 0.775 grams of bis[tetra-n-heptyl)ammonium] tungstate and 27.67 grams of toluene. A two-phase reaction medium resulted and the mixture was continuously stirred to maintain a dispersion of the phases. The reaction mixture was heated to about 140° C. for about 3 hours. During the reaction the pressure increased to about 155 psig and dropped to about 50 psig. The reactor was then cooled with cooling water and then ice water to about 2° C. The aqueous layer was recovered and analyzed to contain monoethylene glycol (68% selectivity), diethylene glycol (26% selectivity) and triethylene glycol (6% selectivity).

EXAMPLE 3

A 50 milliliter, round bottom, glass flask was charged with 10.0 grams of bis(triphenylphosphine)iminium vanadate and 10 milliliters of dichloromethane. The solution was cooled to below 10° C., and 6.91 grams of ethylene oxide (about 0° C.) were then added. After weighing the flask, 6.91 grams of distilled water (about 0° C.) were added to form a two-phase reaction mixture. The mixture was stirred rapidly and refluxed (about 35° C.) under a dry ice/acetone condenser for about 7 hours. The mixture was then allowed to stand at ambient temperature overnight. The aqueous layer was then removed from the organic layer and analyzed to contain monoethylene glycol. No diethylene or triethylene glycol was detected.

EXAMPLE 4

A stirred, 50 milliliter, round bottom, glass flask, equipped with a condenser was charged with 1.0 grams of bis[bis(triphenylphosphine)iminium] molybdate, 5 milliliters of cyclohexene oxide, 1.0 milliliter of distilled water and 5.0 milliliters of 1,1,2-trichloroethane. The mixture was heated to reflux (at ambient pressure) while cooling the condenser with dry ice/acetone for three hours. The heating and stirring was stopped and reinitiated about 15 to 16 hours later and continued for about 7.5 hours. A brown-colored solution was produced. Water and cyclohexane oxide were removed from the mixture under vacuum (about 1 to 2 L millibars absolute) at about 35° C. to 40° C. A white solid condensed on the side of the flask. The solid had a melting point of about 100.5° C. to 101.5° C. Analysis by infrared spectroscopy indicated that the product was exclusively 1,2-trans-dihydroxycyclohexane.

EXAMPLES 5 TO 9

In these examples, the following general procedure was used. Into the reactor were introduced a previously prepared solution of the organometalate in solvent using vacuum to assist in the transfer. The water was then charged and the autoclave purged with nitrogen and vented. Cooled ethylene oxide (liquid) was injected into the autoclave under nitrogen pressure. The reaction menstruum was stirred at a stirrer rotation rate of about 800 rpm. The autoclave was pressurized to about 3.5 atmospheres absolute, heated and then maintained at substantially a constant temperature for about one hour. The pressure was allowed to rise. After cooling, a portion of the aqueous phase was withdrawn for analysis. The details of the examples are provided in Table I.

TABLE I

| Example | Metalate Anion-Containing Material | | Water, g | CH$_2$Cl$_2$, g | Ethylene Oxide, g | Temp. °C. | Selectivity to MEG, % |
| --- | --- | --- | --- | --- | --- | --- | --- |
| | Identity | Amount, g | | | | | |
| 5 | (PPN) VO$_3$* | 8.3 | 33.0 | 33.0 | 33.0 | 140° C. | 73.7% |
| 6 | (PPN)$_2$ MoO$_4$** | 8.3 | 33.0 | 33.0 | 34.0 | 140° C. | 86.7% |
| 7 (control) | — | — | 33.0 | 33.0 | 33.0 | 140° C. | 58.7% |
| 8 (control) | Na$_2$MoO$_4$*** | 1.38 | 33.0 | 33.0 | 34.0 | 140° C. | 87.4% |
| 9 | (PPN)$_2$MoO$_4$ | 7.9 | 33.0 | 33.0 | 33.0 | 100° C.**** | 83.4% |

*bis(triphenylphosphine)iminium metavanadate
**bis[bis(triphenylphosphine)iminium]molybdate
***preferentially soluble in water
****reactor temperature maintained for about two hours

EXAMPLES 10 TO 13

In these examples the following general procedure was used. A stock solution of ethylene oxide (33 grams) and water (71 grams) was prepared in syrum bottle and maintained at about 2° C. A separate stock solution of toluene (10 grams) and bis(tetrahexylammonium)-molybdate (BTHAM) (4.5 grams) was prepared in 120 cubic centimeter syrum bottles at room temperature (about 22° C.). Aliquots of each stock solution were introduced into chilled (about 2° C.) stainless steel tubular microreactors (exterior dimensions of about 9.6 millimeters by 76 millimeters) that are capable of being immersed in a constant temperature bath. The microreactors were purged with nitrogen prior to the introduction of the materials. After introducing the materials, the reactors were sealed and immersed in the bath while under a reciprocating motion to promote agitation. After about one hour, the microreactors were withdrawn from the bath and cooled to about 0° C. in an ice bath. Samples of the aqueous phase were withdrawn and analyzed. The details of the examples are provided in Table II.

TABLE II

| Example | Water, g | Toluene, g | Ethylene Oxide, g | BTHAM, g | Temp., °C. | Selectivity to MEG, % |
| --- | --- | --- | --- | --- | --- | --- |
| 10 | 0.38 | 1.42 | 0.17 | 0.64 | 110° C. | 97.3 |
| 11 | 1.47 | 0.36 | 0.69 | 0.16 | 110° C. | 91.5 |
| 12 | 0.38 | 1.42 | 0.17 | 0.64 | 140° C. | 98.5 |
| 13 | 1.47 | 0.36 | 0.69 | 0.16 | 140° C. | 91.2 |

EXAMPLE 14

Into an evacuated (about 10 millibar absolute) glass vessel at room temperature, containing one gram of bis(triphenylphosphine)iminium metavanadate, was introduced a mixture of 50 weight percent ethylene oxide and 50 weight percent argon until the pressure in the vessel had increased by about 500 to 550 millibars. Then a mixture of 10 milliliters of water and 50 milliliters of 1,1,2-trichloroethane was syringed into the reactor. The reactor was heated to reflux while stirring magnetically. After about one hour a circulating pump was turned on. The system was shut down after about 3 hours and allowed to sit overnight. Then an additional 4 milliliters of ethylene oxide were added and the system restarted. After about 2 hours, the solvent layer was distilled under vacuum and heat with several washings of 1,1,2-trichloroethane (72.3 grams of solvent layer recovered). An aqueous layer of 41.4 grams was obtained and a sample was analyzed to contain monoethylene glycol.

EXAMPLE 15

Under an argon atmosphere 5.28 grams of tetrahexylammonium molybdate were added to a 100 milliliter glass flask. The flask was then cooled to about 10° C. and 9.66 grams of ethylene oxide were poured into the flask and then about 9.61 grams of distilled water (about 0° C.) were added. The flask was purged with argon and then refluxed using dry ice in an acetone cooled condenser for 5 hours then the condenser was allowed to warm to room temperature. The apparatus was allowed to stand overnight. About 9 milliliters of water were added with shaking and then about 30 milliliters of toluene were added and three distinct phases formed. The aqueous layer was found to contain monoethylene glycol.

EXAMPLES 16 TO 25

Substantially the same procedure described in Examples 1 and 2 was employed in these examples. The details are provided in Table III. In all examples except 18 and 19, the stirring was at about 420 rpm. In example 18, the stirrer rate was about 840 rpm and in example 19, 300 rpm. In all but example 20, the maximum temperature of the reaction menstruum was about 140° C. In example 20, it was about 170° C.

Table V, which follows, provides a further expansion of the principles illustrated in the preceding examples.

TABLE V

| Example No. | Metalate Anion-Containing Material | Alkylene Oxide | Mole Ratio/ Metalate:Oxide | Solvent | Predominant Product |
|---|---|---|---|---|---|
| 27 | tetra-n-hexylammonium vanadate (pH 10) | ethylene oxide | 1:5 | dichloromethane | monoethylene glycol |
| 28 (Comparison) | tetra-n-hexylammonium rhenate | ethylene oxide | 1:1 | toluene | monoethylene glycol (no enhanced selectivity) |
| 29 | bis[bis(triphenyl-phosphonium)iminium] molybdate | propylene oxide | 0.005:1 | dichloromethane | propylene glycol |
| 30 | bis[bis(triphenyl-phosphonium)iminium] molybdate | styrene oxide | 0.01:1 | dichloromethane | 1,2-dihydroxyethylbenzene |
| 31 | bis[bis(triphenyl-phosphonium)iminium] molybdate | 1,2 epoxybutane | 0.006:1 | dichloromethane | 1,2-butanediol |

TABLE III

| Example | Ethylene Oxide, g | Water | Metalate-Anion Containing Material | | Solvent | | Selectivity to MEG, % |
|---|---|---|---|---|---|---|---|
| | | | Identity | Amount, g | Identity | Amount | |
| 16 | 16.0 | 16.2 | A | 0.81 | T | 30 ml | 76.2% |
| 17* | 16.0 | 16.1 | A | 0.80 | T | 30 ml | 79.4% |
| 18 | 16.3 | 16.2 | A | 0.81 | T | 30 ml | 74.6% |
| 19 | 16.3 | 16.4 | A | 0.81 | T | 30 ml | 75.7% |
| 20 | 16.4 | 16.6 | A | 0.82 | T | 30 ml | 78.9% |
| 21 | 16.0 | 15.5 | A | 4.90 | T | 30 ml | 93.7% |
| 22** | 16.2 | 16.3 | C | 1.0 | H | 30 g | 61.8% |
| 23 | 15.6 | 15.5 | B | 1.5 | H | 30 g | 64.8% |
| 24 | 15.8 | 15.2 | B | 1.5 | E | 30 g | 64.2% |
| 25 | 14.9 | 15.1 | A | 1.5 | M | 45 g | 87.5% |

*Heating for ½ hour, insufficient time for complete reaction of ethylene oxide.
**Organic phase contains catalyst layer Metalate Anion-Containing Materials
A  Bis(tetra-n-hexyl-Ammonium)molybdate
B  Bis(tetra-n-octadecyl-Ammonium)molybdate
C  Bis(tetra-n-dodecyl-Ammonium)molybdate Solvent
H  Hexane
E  Dibutyl ether
M  20g toluene and 25g triphenylphosphine oxide
T  Toluene

EXAMPLE 26

Substantially the same procedure described in Example 1 was employed except that the toluene-containing layer was recovered from a reaction medium and was used in a subsequent reaction medium. The aqueous layer from the reaction yielding the toluene was extracted twice with about 10 milliliters of toluene and a portion of the rinse toluene was also used in the subsequent reaction.

The first run employed about 1.5 grams of bis(tetra-n-hexylammonium)molybdate. The details are provided in Table IV.

The low selectivities in runs 2 to 5 are believed to be due to difficulty in obtaining a good and rapid phase separation. A more preferable solvent would be, e.g., dichloromethane.

TABLE IV

| Run | Ethylene Oxide, g | Water, g | Recycle Toluene, g | Rinse Toluene, g | Selectivity to MEG, % |
|---|---|---|---|---|---|
| 1 | 16.0 | 15.4 | (Fresh Toluene, 30 g) | | 82.3% |
| 2 | 15.8 | 15.5 | 27.8 | 3.6 | 43.2% |
| 3 | 15.6 | 15.3 | 28.6 | 2.9 | 32.2% |
| 4 | 15.8 | 15.4 | 26.4 | 5.1 | 44.2% |
| 5 | 15.5 | 15.5 | 30.0 | 1.8 | 47.0% |

EXAMPLE 32 (Comparative)

The reactor was charged with 15.19 grams of distilled water, 30 milliliters of toluene and (after cooling to about 0°–5° C.) 14.97 grams of ethylene oxide. The mixture was stirred and heated to about 140° C. for about 3.5 hours, cooled to about 2° C. in ice water. The aqueous layer was recovered and analyzed to contain monoethylene glycol (56% selectivity), diethylene glycol (33% selectivity) and triethylene glycol (11% selectivity).

It is claimed:

1. A process for making alkylene glycols from alkylene oxide and water comprising contacting the alkylene oxide with a water-containing reaction menstruum under conditions sufficient to form alkylene glycol, said water-containing reaction menstruum comprising an aqueous phase; a water-immiscible liquid phase and a selectivity-enhancing amount of a selectivity-enhancing, dissociatable metalate anion-containing material comprising an organometalate having an organic-containing cation, wherein said water-immiscible liquid phase has a greater concentration of said metalate anion-containing material than does the aqueous phase.

2. The process of claim 1 wherein the water-immiscible liquid phase comprises a substantially water-insoluble organic solvent.

3. The process of claim 2 wherein the metalate anion-containing material is substantially insoluble in water at 25° C.

4. The process of claim 2 wherein the aqueous phase comprises the continuous phase of the reaction menstruum.

5. The process of claim 2 wherein the water-immiscible liquid phase comprises the continuous phase of the reaction menstruum.

6. The process of claim 2 wherein the metalate anion has the formula $[(A)_qM(O)]^a$ where M is a polyvalent metal having a functional positive oxidation state; A represents one or more substituents to fill the remaining valencies (q) of M, and a is the negative charge of the anion.

7. The process of claim 6 wherein the metalate anion is selected from the group consisting of vanadate, molybdate and tungstate.

8. The process of claim 6 wherein the alkylene oxide has the formula

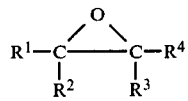

wherein each of $R^1$, $R^2$, $R^3$ and $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbons.

9. The process of claim 8 wherein the alkylene oxide is ethylene oxide.

10. The process of claim 2 wherein the mole ratio of metalate anion to alkylene oxide is between about 0.1:100 to 1:1.

11. The process of claim 9 wherein the mole ratio of metalate anion to ethylene oxide is between about 0.1:100 to 1:1.

12. The process of claim 6 wherein the organometalate is preferentially soluble in the organic solvent as compared to water at 25° C.

13. The process of claim 12 wherein the organic-containing cation is represented by the formula $$[(R^0)_m Y_n]^{x+}$$

wherein Y is a polyvalent element which is an ionic charge carrying center; $R^0$ is hydrogen or hydrocarbyl-containing substituent with the proviso that Y has at least one $R^0$ which contains a hydrocarbyl substituent; m is the average number of electron pairs shared by Y with the total $R^0$ groups; and n is the number of charge carrying centers, wherein m, n and x are related by the equation $x=n(V-m)$ in which V is the average functional oxidation state of Y wherein each electron pair used by each Y in bonding to R is given the value of 1 and the formal oxidation state of Y is the sum of the electron pairs bonding to $R^0$ and x/n, and x is an integer of 1 or 2.

14. The process of claim 13 wherein the metalate anion is selected from the group consisting of vanadate, molybdate and tungstate.

15. The process of claim 14 wherein the organic-containing cation comprises an ammonium cation.

16. The process of claim 15 wherein the ammonium cation comprises a tetraalkyl ammonium cation.

17. The process of claim 14 wherein the organic-containing cation comprises phosphonium cation.

18. The process of claim 17 wherein the phosphonium cation comprises a tetralkyl phosphonium cation.

19. The process of claim 14 wherein the organic-containing cation comprises a bis(trisubstituted phosphine)iminium.

20. The process of claim 14 wherein the mole ratio of water to alkylene oxide is from about 1:1 to 20:1.

21. The process of claim 20 wherein the mole ratio of water to alkylene oxide is from about 1:1 to 10:1.

22. The process of claim 14 wherein the alkylene glycol is preferentially soluble in the aqueous phase as compared to the water-immiscible phase.

23. The process of claim 2 wherein the mole ratio of water to alkylene oxide is from about 1:1 to 10:1.

24. The process of claim 23 wherein the water-immiscible phase and the aqueous phase are separated after contact with alkylene oxide and alkylene glycol is recovered from the aqueous phase.

25. The process of claim 24 wherein at least a portion of the separated water-immiscible phase is subsequently contacted with water and alkylene oxide.

26. A process for making alkylene glycols from alkylene oxide and water comprising contacting the alkylene oxide with a water-containing reaction menstruum under conditions sufficient to form alkylene glycol, said water-containing reaction menstruum comprising an aqueous phase; a water-immiscible liquid phase comprising a substantially water-insoluble organic solvent which is at least one member selected from the group consisting of benzene, toluene, xylene, dichloromethane and 1,1,2-trichloroethane; and a selectivity-enhancing amount of a selectivity-enhancing, dissociatable metalate anion-containing material comprising an organometalate having an organic-containing cation, wherein said water-immiscible liquid phase has a greater concentration of said metalate anion-containing material than does the aqueous phase.

* * * * *